(12) United States Patent
Pan et al.

(10) Patent No.: US 6,858,648 B2
(45) Date of Patent: Feb. 22, 2005

(54) LAETISPICINE AND LAETISPICINE ANALOGUES, METHODS OF USE AND PREPARATION

(75) Inventors: Sheng-li Pan, Shanghai (CN); Fu-gang Qian, Shanghai (CN); Ren Wen, Shanghai (CN); Jing Xie, Shanghai (CN); Jun Wang, Shanghai (CN); Yi-ci Shao, Shanghai (CN)

(73) Assignees: Fudan University, Shanghai (CN); Shanghai Institute of Pharmaceutical Industry, Shanghai (CN)

( * ) Notice: Subject to any disclaimer, the term of this patent is extended or adjusted under 35 U.S.C. 154(b) by 0 days.

(21) Appl. No.: 10/616,605

(22) Filed: Jul. 10, 2003

(65) Prior Publication Data

US 2004/0053994 A1 Mar. 18, 2004

(30) Foreign Application Priority Data

Jul. 12, 2002 (CN) ........................... 02136003 A

(51) Int. Cl.[7] ..................... C07D 317/60; A61K 31/343
(52) U.S. Cl. ..................... 514/464; 514/466; 549/441
(58) Field of Search ..................... 549/441, 439, 549/440, 442, 445, 447; 514/464, 466

(56) References Cited

U.S. PATENT DOCUMENTS

| | | |
|---|---|---|
| 5,536,506 A | 7/1996 | Majeed |
| 5,693,327 A | 12/1997 | Shah |
| 6,080,410 A | 6/2000 | Bewicke |
| 6,312,735 B1 | 11/2001 | Niazi et al. |
| 6,346,539 B1 | 2/2002 | Raman |

OTHER PUBLICATIONS

Banerji et al. Phytochemistry, vol. 59, No. 8, p. 897–901 (Apr. 17, 2002).*

Porsolt Rd, Bertin A, Jalfre M (1977) Behavioural despair in mice: A primary screening test for antidepressants. Arch Int Pharmacodyn 229:327–336.

Porsolt Rd, Le Pichon M, Jalfre M (1977) Depression: A new animal model sensitive to antidepressant treatments. Nature 266:730–732.

* cited by examiner

*Primary Examiner*—Bernard Dentz
(74) *Attorney, Agent, or Firm*—Yuan Qing Jiang

(57) ABSTRACT

A compound having the following Formula:

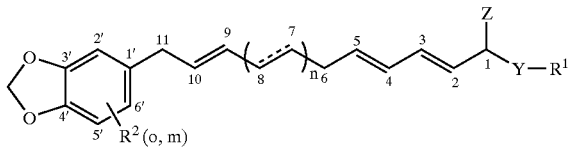

wherein R1, R2, Z, and Y are defined herein, and methods of preparation and application for treating mental disorders and inflammation are provided therewith.

14 Claims, 2 Drawing Sheets

NMR EXPERIMENT RESULTS

| Carbon Atom | $^{13}$CNMR (δppm) | $^{1}$HNMR (δppm) | Multiplicity (J in HZ) | COSY ($^{1}$H—$^{1}$H) |
|---|---|---|---|---|
| 1 | 166.38 | | | |
| 2 | 124.47 | 5.96 | d (15.2) | H-3,H-4 |
| 3 | 140.45 | 7.10 | dd(15.2,10.8) | H-2,H-4 |
| 4 | 130.01 | 6.18 | dd(15.2,10.6) | H-3,H-5 |
| 5 | 141.95 | 6.06 | dt(14.8,6.8) | H-4,H-6 |
| 6 | 32.99 | 2.17 | br quartet | H-7,H-5 |
| 7 | 29.50 | 1.52 | m | H-6,H-8 |
| 8 | 32.64 | 2.06 | m | H-7,H-9 |
| 9 | 131.91 | 5.54 | m | H-8,H-11 |
| 10 | 130.80 | 5.54 | m | H-8,H-11 |
| 11 | 39.32 | 3.25 | d(5.2) | H-10,H-2', H-6' |
| 1' | 135.82 | | | |
| 2' | 108.89 | 6.69 | m | O-CH$_2$-O |
| 3' | 148.72 | | m | |
| 4' | 146.83 | | m | |
| 5' | 109.70 | 6.74 | m | H-6',O-CH$_2$-O |
| 6' | 122.05 | 6.64 | m | H-5',H-2', H-11 |
| 1" | 47.45 | 3.08 | t(6.6) | H-2", NH |
| 2" | 29.22 | 1.78 | 7 line multiplet (6.4) | H-3", H-4", H-1" |
| 3",4" | 20.56 | 0.9 | d(6.8) | H-2" |
| O-CH$_2$-O | 101.78 | 5.94 | s | H-5',H-2' |
| NH | | 7.1 | br | H-1" |

FIG. 1

LAETISPICINE AND LAETISPICINE ANALOGUES, METHODS OF USE AND PREPARATION

FIELD OF INVENTION

This invention relates to a chemical compound, and more particularly to Laetispicine and Laetispicine analogues, methods of use and preparation.

BACKGROUND OF INVENTION

Mental disorders are chronically arrested or incomplete development of mind, psychopathic disorder and any other disability of mind that interfere with a person's life. Mental disorders are diseases that affect people of all age groups world wide, causing personal suffering, family misfortune and social burden. Depression, psychopathic disease and Alzheimer's disease are a few examples of mental disorders.

Currently, the most common forms of medication for treating personality-disorder such as depression and psychopathic patients are chemically synthesized compounds such as neuroleptics, antidepressants, lithium, and benzodiazepines. However, administrating these compounds to patients brings the inevitable drug side effects to the patients, which severely limits the use of the drugs. The risk of drug interaction is also common for patients taking anti-psychotic medications in combination with other drugs. Some anti-psychotic medications interfere with the action of anti-hypertensive medications (taken for high blood pressure), anti-convulsants (taken for epilepsy) and medications used for Parkinson's disease. Some anti-psychotic medications add to the effects of alcohol and other central nervous system depressants, such as antihistamines, anti-depressants, barbiturates, some sleeping and pain medications, and narcotics.

For example, neuroleptics can have both a tranquillizing effect on disturbed behavior, most notably persistent tension, anger and hostility and a specific anti-psychopathic effect. These drugs block various dopamine receptors (nervous system chemicals) in the brain. In addition to limiting psychosis, however, lower dopamine levels also affect the motor system, causing unwanted muscular side effects.

Antidepressants, such as selective serotonin reuptake inhibitors (SSRIs), tricyclics and monoamine oxidase inhibitors (MAOIs) have been used with patients who display persistent dysphoric mood and major or atypical depression, such as panic attacks, mood swings and dysthymia. Some examples of SSRIs are fluoxetine (Prozac), fluvoxamine (Luvox), paroxetine (Paxil), and sertraline (Zoloft). The common side effects of SSRIs include sleep disturbance, headaches, gastrointestinal problems and sexual dysfunction. Side effects for patients taking tricyclics are anticholinergic such as constipation, dry mouth, blurred vision and urinary retention, histaminergic such as sedation and weight gain or adrenergic such as orthostatic hypotension. The side effects of MAOIs include orthostatic hypotension, weight gain, sexual dysfunction and insomnia. When taking any nonspecific irreversible MAOI, patients must maintain a restrictive tyramine-free diet, and hypertensive crisis is risked if adherence to that diet is not maintained. The MAOIs also introduce a risk for serious drug-drug interactions (e.g., sympathomimetic drugs and meperidine).

Lithium is also used in the treatment of psychopathic patients because it can reduce impulsive, explosive and emotionally unstable behaviors. However, lithium is known for its very small range between an effective dose and a toxic one.

Benzodiazepines are known among clinicians to be highly effective in their control of anxiety states and insomnia. But benzodiazepines are also known to produce physical dependency, manifested by a withdrawal syndrome on abrupt discontinuation. Even with gradual tapering, it may be difficult for some patients to discontinue Benzodiazepines therapy.

Recent development in treating Alzheimer's disease has been focused on a group of drugs known as cholinesterase inhibitors or anti-cholinesterase drugs. These drugs reduce the breakdown of acetylcholine in the brain. Acetylcholine is a chemical substance that occurs naturally in the brain and enables nerve cells in the brain to pass messages to each other. Research has shown that many people with Alzheimer's disease have a reduced amount of acetylcholine, and it is thought that the loss of this chemical may result in deterioration of memory. These drugs include Reminyl (also called galantamine), Aricept (donepezil hydrochloride) and Exelon (rivastigmine). Side effects may include diarrhea, nausea, insomnia, fatigue and loss of appetite. It is important to realize that these drugs are not a cure, and may only stabilize some of the symptoms of early to mid stage Alzheimer's disease for a limited period of time.

In order to avoid the side effects of chemically synthesized drugs, herb medicine is welcomed in the treatment of mental disorders as an alternative and supplemental source of new medicine. Herb medicine is natural and usually non-prescription. The advantages of herbal medicine are its mild side effect, less dependent production and low risk of interaction with alcohol or other medications. A representative herb for treating depression is St. John's Wort. St. John's Wort is an herb that has been used for centuries for medicinal purposes, including treating depression. The composition of St. John's Wort and how it might work are not well understood. Some scientific evidence shows that St. John's Wort is useful for treating mild to moderate depression. However, recent studies suggest that St. John's Wort is of no benefit in treating major depression of moderate severity. More research is required to determine whether St. John's Wort has value in treating other forms of depression. The major disadvantage of herb medicine is disputed effectiveness, due to multiple ingredients and unpurified effective ingredients.

In view of St. John's Wort controversial therapeutic result, it is necessary to search for new and effective herbs for treating mental disorders. Further research and development work is also called for. Future work includes but not limited to, isolating of the herb's effective ingredients to prove its pharmacological value, purifying the isolated ingredients, understanding the pharmacological principle of the effective ingredients, modifying the chemical structure of the effective molecules to search for better drugs, establishing of animal models for screening and testing the molecules and obtaining pharmacodynamic and pharmacokinetic data, and clinically testing the new drug.

SUMMARY OF THE INVENTION

The present invention provides new compounds, and methods for producing and using the compounds to treat mental disorders.

In a first aspect, the invention features new compounds having the following general chemical structure of Formula I:

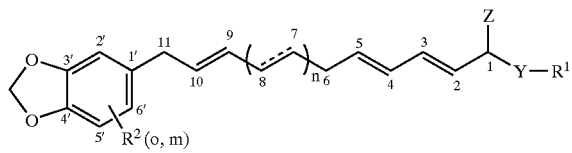

wherein $R^1$ is hydrogen, $C_{1-10}$ alkyl or aromatic cyclic group, $R^2$ is selected from the group consisting of hydrogen, $OR^3$, $NH_2$, $NHR^3$, and halogen, Z is selected from the group consisting of =O, OH, $NHR^3$, SH, and $SR^3$, wherein $R^3$ is $C_{1-10}$ alkyl or aromatic cyclic group, $(C_7-C_8)_n$ includes at least one single bond or at least one double bond, and n is an integer having a value of from 0 to 10. In one embodiment, Y is selected from the group consisting of NH, $NR^3$—, O, and S.

In one embodiment, the invention provides a Laetispicine compound having the following chemical structure of Formula II:

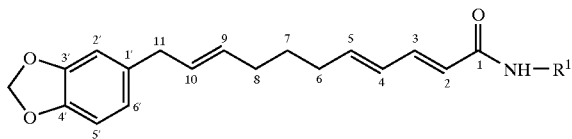

wherein $R^1$ is isobutyl (—$CH_2$—$CH(CH_3)_2$).

In another aspect, the invention features a pharmaceutical composition in unit dose form suitable for treating mental disorders. The composition comprises effective amount of the compound of Formula I or II or an analogue thereof. The composition may also comprise at least one pharmaceutically acceptable excipient. The compound can be chemically modified salt or prodrug. The composition is useful for treating a wide variety of mental disorders, including, for example, depression, psychopathic disease, and Alzheimer's disease.

Yet in another aspect, the present invention provides a method of obtaining the compound of Formula I or II. The method includes isolating, purifying and chemically synthesizing the compound from Piper laetispicum C. DC of Piperaceae family.

The present invention additionally provides various embodiments of compounds, and methods for producing and using the compounds to treat mental disorder and to alleviate inflammation and pain.

Unless otherwise defined, all technical or scientific terms used herein have the same meaning as commonly understood by one of ordinary skilled in the art to which this invention belongs. Although methods and materials similar or equivalent to those described herein can be used in the practice or testing of the present invention, suitable methods and materials are described below. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 shows a table of NMR spectrum data for Laetispicine.

DETAILED DESCRIPTION OF THE INVENTION

Figure 2:
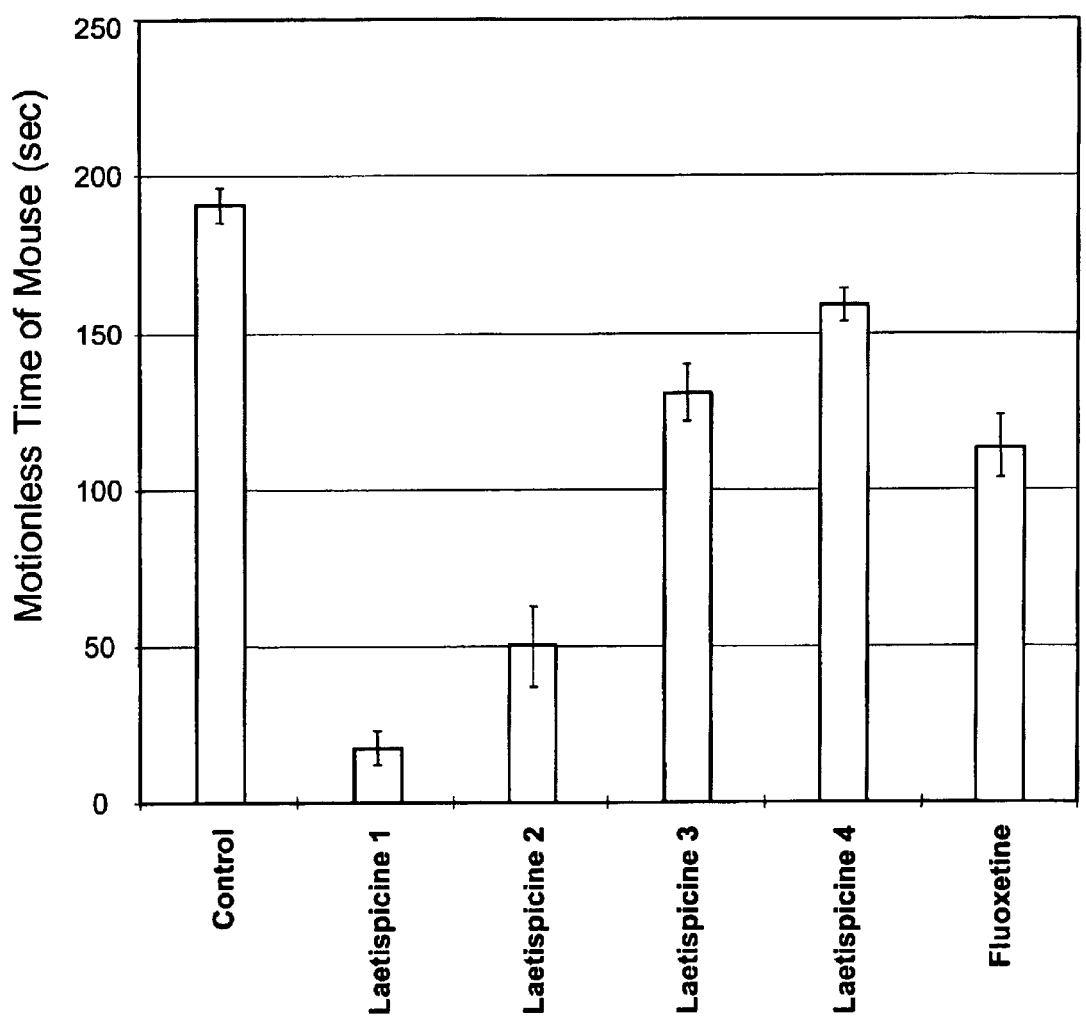
FIG. 2 shows Laetispicine anti-depression effect on mouse forced swimming experiment.

In a first embodiment, the present invention provides novel compounds having the following general chemical structure of Formula I:

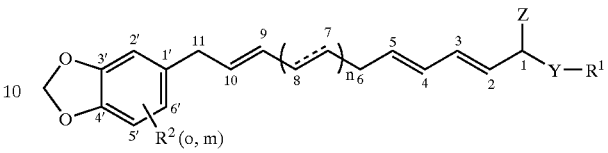

wherein $R^1$ is hydrogen, $C_{1-10}$ alkyl or aromatic cyclic group, $R^2$ is selected from the group consisting of H, $OR^3$, $NH_2$, $NHR^3$, and halogen (F, Cl, Br, I), Z is selected from the group consisting of =O, OH, $NHR^3$, SH, and $SR^3$, wherein $R^3$ is $C_{1-10}$ alkyl or aromatic cyclic group, C7–C8 can be substituted by an alkyl chain in which the n is 0 to 10, and some of the single bonds can be substituted by some double bonds. In one embodiment, Y is selected from the group consisting of NH, $NR^3$—, O, and S.

The compounds described by Formula I and its analogues can be produced from isolation, purification and modification of a substance from natural herbs. For example, Piper laetispicum C. DC is an herb growing in China and part of Southeast Asia, where herb medicine has been used in human society for long time. Piper laetispicum C. DC, which is known as Da Ye Ju in China, is one of the species in Piperaceae family. Traditionally, Chinese have been using the plant for alleviating the symptoms of rheumatism. It has been proved that the plant is safe and mild of side effect in its long time clinical use.

Individual species of Piperaceae family growing in distinctive regional climate in the world have their unique characters. Possible explanation for the difference of the species is that the regional soil, whether and bio-ecological condition put an evolutional pressure on the plant, and the resultant gene mutation leads the plant developing its characteristic chemical composition to cope with the environmental demand. For example, two of the Piperaceae family members, Piper Nigrum L. (black pepper) and Piper Longum L. (long pepper), are part of ingredients in an herb composition for treating skin disorders such as psoriasis, eczema and lichen planus as disclosed in U.S. Pat. No. 5,693,327. Later on, U.S. Pat. No. 6,346,539 disclosed that Piperine, a chemical isolated from the fruit of Piper Nigrum L. (black pepper) and Piper Longum L. (long pepper), might be effective in the treatment of skin conditions such as vitiligo and skin cancer. Piperine is also proposed to be used to improve gastrointestinal absorption and systemic utilization of nutrients in U.S. Pat. No. 5,536,506.

Piperaceae family is a rich source of herbs. Different herbs in Piperaceae family have been used to treat different disease. In addition, different parts of the herb plant may have different function in the treatment. For example, betel leaf (Piper betle L.) is another member of Piperaceae family. It is called Ju Jiang Ye in China. One of the most popular uses of betel leaf is in the composition called, "betel," which is a compound of natural substances chewed for its psychostimulating effects. Betel is composed of the nut of the areca palm (Areca catechu), the leaf of the betel pepper (Piper betle), and lime (calcium hydroxide). According to U.S. Pat. No. 6,312,735, approximately 300 million persons chew betel regularly throughout the western Pacific basin and south Asia. When betel is chewed, it produces mild psychoactive and cholinergic effects. Betel use is associated with oral leukoplakia, submucous fibrosis, and squamous cell carcinoma. Use of betel is discouraged in Western countries because of its alleged carcinogenic and perceived dysesthetic properties. Yet the inventors of U.S. Pat. No. 6,312,735 discovered that betel leaf extract might be used to remove warts and moles, which is another example of medicinal use of the herb.

*Piper methysticum* Forst, another species of the Piperaceae family and commonly known as Kava-kava root, is now popular in the West. The part of the herb for medicinal use consists of the dried rootstock and/or shoots. According to U.S. Pat. No. 6,080,410, the Kava root extract is known to induce general relaxation in humans when orally ingested. An aqueous macerate of the Kava root known as "kava" or "kawa" has been used on islands in the South Pacific in social gatherings and religious rituals for three thousand years.

In recent years, the Kava plant has been scientifically scrutinized with many of its active constituents being identified. The psychoactive ingredients of the Kava root have been identified as kavalactones, also known as kavapyrones. A total of fifteen kavalactones have been identified to date, including kavain, dihydrokavain (a.k.a. marindinin), methysticin, dihydromethysticin, yangonin, and desmethoxyyangonin. The particular kavalactones in a Kava root extract vary depending upon its origin. Further, the particular kavalactones present depend upon whether, in addition to rhizome parts, roots and stems of the plant are included in the extract.

In another embodiment according to the present invention, Laetispicine is isolated and purified from herb *Piper Laetispicum* C. DC. The chemical structure of Laetispicine is shown in Formula II:

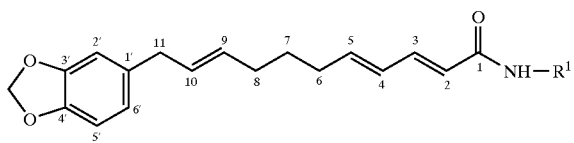

wherein $R^1$ is isobutyl (—$CH_2$—$CH(CH_3)_2$). The chemical name of Laetispicine (Formula II) is N-isobutyl-11-(3,4-methylendioxyphenyl)-2E,4E,9E-undecatrienamide. The molecular Formula of Laetispicine is $C_{22}H_{29}NO_3$. Laetispicine is colorless, needle shaped crystals, with the melting point of 93–94° C. NMR data (FIG. 1) indicate that Laetispicine is a long carbon atom chain with a NH group and some double bonds, attached with a benzene ring with oxygen groups. Animal study showed that the anti-depression effect of Lactispicine is 5 times of that of Fluoxetine (Prozac) (FIG. 2) and the anti-inflammation and pain relieving effect of Lactispicine is equivalent to the effect of Aspirin (Table 2). The details of isolation and purification processes for producing Lactispicine are described in Experiment 1. Methods for obtaining the compounds of Formulas I, II and their analogues are also provided. For example, Formulas II can be extracted from *Piper laetispicum* C. DC of Piperaceae family, and then it is purified and crystallized. Such extraction techniques include an ethanol extraction followed by an ethyl acetate extraction. Purification of the extracted substance is performed on a silica gel column with standard elution techniques. Formula I and other analogues will be produced by methods of chemical modification of Formula II. Such methods include but not limited to addition, substitution, oxidation, reduction and modification. Other methods of producing the compounds from Piperaceae will be apparent to those of skilled in the art. For example, modifications in column packing, elution buffers, flow rates for eluting the compound may all be modified or changed. Such process modifications are routine to those of skilled in the art.

Variation of Laetispicine derives a more general form of the compound (referring to Formula I). For example, =O at position 1 can be replaced by OH, $NH_2$, $NHR^3$, SH, or $SR^3$. NH can be substituted by $NHR^3$, O, or S. Such modifications are within the skill of those in the art. Additionally, modification of the stereochemistry of the above Formulas is also within the skill of those in the art. For example, alkyl chain, double bonds and stereochemical substitutions are applicable to carbons 7–8 of the present compounds so long as the compound retains its biological activity. By "biological activity" is meant the ability of the compound to inhibit, suppress or modulate mental disorders and pain.

Various Laetispicine analogues may be made from Piperaceae using a range of chemistries, or from chemical synthesis. Additionally derivations will be recognized and are routine to those of skilled in the art.

The structures of Formula I, II and their analogues are capable of forming pharmaceutically acceptable salts, including acid addition salts and base salts, as well as solvates, such as hydrates and alcoholates. All of these pharmaceutical forms are contemplated by this invention and are included herein. Acid addition salts are readily formed when a Formula I, II or their analogues compound contains amino substitute groups, or when nitrogen atoms are present. Base salts can be formed when carboxylic acid substitute groups are present.

Pharmaceutically acceptable acid addition salts of the compounds of Formula I, II and their analogues include salts derived from inorganic acids such as hydrochloric, nitric, phosphoric, sulfuric, hydrobromic, hydriodic, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include sulfate, pyrosulfate, bisulfate, sulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like, gluconate, and galacturonate.

The acid addition salts of basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

The base addition salts of acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, "pharmaceutically acceptable salts" refer to analogues of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Prodrugs" are also encompassed by the present specification and are intended to include any covalently bonded carriers which release the active parent drug according to Formula I, II and their analogues in vivo when such prodrug is administered to a mammalian subject, the mammal may be a human. Prodrugs of a compound of Formula I, II and their analogues are prepared by modifying functional groups present in the compound in such a way that the modifications are cleaved, either in routine manipulation or in vivo, to the parent compound. Prodrugs include compounds of Formula I, II and their analogues wherein a hydroxy, amino, or sulfhydryl group is bonded to any group that, when the prodrug or compound of Formula I, II and their analogues is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula I, II, their analogues and the like.

The invention provides methods of treating mental disorder such as depression, psychopathic disease or Alzheimer's disease in a subject comprising administering a compound of Formula I, II or their analogues. In addition, the method of treating pain and inflammation in a subject comprising administering a compound of Formula I, II or their analogues. Detailed examples and animal experiments are given in EXPERIMENT 3 and 4. The subject is a mammal or a human. The compounds can be administered orally, intravenously, subcutaneously, intramuscularly, or through inhalation depending on the need of treating mental disorder and on various indications. For example, oral administration is used for mental disorder patients who are cooperative, while intravenously administration is used for patients in an emergency situation.

Laetispicine and its analogues act as anti-depression and pain relieving agents. Without being bound by any particular theory or biochemical mechanism, Laetispicine and its analogues are able to inhibit and eliminate the factors causing depression and pain in a subject. These compounds may be eliminated and excreted through normal metabolic pathways of the subject. The actual dosage of Laetispicine and its analogues thereof, Formulation or composition that modulates mental disorder and pain depends on many factors, including the size and health condition of an individual. However, one of ordinary skilled in the art can use pharmacodynamic and pharmacokinetic methods and techniques for determining clinical dosages to determine the appropriate dosage to use.

Compounds of the invention may be Formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Sustained release compositions are also encompassed by the present invention. Compositions for other routes of administration may be prepared as desired using standard methods.

A compound of the invention may be conveniently administered in unit dosage form, and may be prepared by any of the methods well known in the pharmaceutical art. Formulations for parenteral administration may contain as common excipients sterile water or saline, polyalkylene glycols such as polyethylene glycol, oils of vegetable origin, hydrogenated naphtalenes, and the like. Other suitable parenteral delivery systems include ethylene-vinyl acetate copolymer particles, osmotic pumps, implantable infusion systems, and liposomes.

The invention also relates to an article of manufacturing containing at least one packaging material and Laetispicine or its analogues thereof contained within the packaging material. Laetispicine and its analogues thereof are therapeutically effective for treating mental disorders or alleviating inflammation and pain in a subject. The packaging material may contain a label or package insert indicating that Laetispicine and its analogues thereof may be used for treating mental disorder or alleviating inflammation and pain in a subject.

In an alternate embodiment, the invention relates to compositions and kits comprising a first chemotherapeutic agent including Laetispicine or its analogues thereof and at least one of second therapeutic agent. The second therapeutic agent is not Laetispicine or its analogues thereof. These compositions are effective to treating mental disorder or inflammation and pain in a subject. Various classes of therapeutic agents, including neuroleptics, antidepressants, lithium, benzodiazepines, cholinesterase inhibitors or anticholinesterase drugs, aspirin, acetaminophen, ibuprofen, ketoprofen, naproxen, may be used in the composition.

The invention will be further described in the following examples, which do not limit the scope of the invention described in the claims.

EXPERIMENT 1

Isolation and Purification of Laetispicine

*Piper laetispicum* C. DC 1,000 gram was crushed and grinded. The grinded plant was added 6 times of its volume of 95% industrial ethanol and heated in a circulating device for 2 hours. It was then cooled down and filtered. The first part of ethanol was collected. The solid leftover after the first filtration was add 4 times of its volume of 95% industrial ethanol, again heated in the circulating device for 2 hours. After it was cooled down and filtered, the second part of ethanol was collected. The first and second parts of ethanol were then pooled together, concentrated by evaporation in low atmospheric pressure in a vacuum device. Fifty grams paste of crude extracts of *Piper laetispicum* C. DC was obtained after evaporation.

The Fifty grams of crude paste of *Piper laetispicum* C. DC was added by 50 ml of water until a concentrated water solution was formed. The *Piper laetispicum* C. DC water solution was extracted by ethyl acetate in 1 to 1 ratio). The extractions were performed 5 times in a heated circulating device. Each extract was collected and cooled down, and pooled together. The ethyl acetate extractions of *Piper laetispicum* C. DC were then evaporated and concentrated. The process produced 10 gram of ethyl acetate extract paste of *Piper laetispicum* C. DC.

The 10 gram of ethyl acetate extract paste of *Piper laetispicum* C. DC was then loaded onto a gradient silica gel column and eluted by using cyclohexane-ethyl acetate (concentration ratio was 5-1 to 3.5-1.5) as eluant. Six fractions of elution were collected and concentrated: Fr. I, Fr. II, Fr. III, Fr. IV, Fr. V, Fr. VI. The elution fraction four Fr. IV was again loaded onto a gradient silica gel column for further elution by using aceton—ether as eluat (concentration ratio was 6-1 to 3-1). After the second gradient elution, four sub-fractions of the fraction four (Fr. IV) elution were collected and concentrated: SubFr. IV-1, SubFr. IV-2, SubFr. IV-3, and SubFr. IV-4. Sub-fraction Fr. IV-3 was crystallized to form 300 milligram of colorless, needle shaped crystal. The crystallized sub-fraction SubFr. IV-3 is compound Formula II, (Laetispicine). Its melting point was m.p. 93–94° C., The molecular Formula $C_{22}H_{29}NO_3$ was derived from $^1$HNMR (400 MHZ, aceton-d6) and $^{13}$C NMR (100 MHZ, aceton-d6) data. The chemical structure of Laetispicine (Formula II) was N-isobutyl-11-(3, 4-methylendioxyphenyl)-2E,4E,9E-undecatrienamide.

EXPERIMENT 2

NMR and UV Spectrum

The structure of the novel compound Formula II, Laetispicine, was determined by extensive NMR and UV spectrum experiments. The same specimen of the compound Formula II, Laetispicine, was used in all the following experiments.

Compound Formula II, Laetispicine, was obtained as colorless needle shaped crystals, m.p. 93–94° C., HRMS (355.1257). MS m/z (R.Int.): 355 (M+, 8.44), 240 (22.36), 220 (100), 135 (83.90), 121 (32.16), 107 (22.67), 91 (30.11), 79 (38.49) 67 (20.91). The UV spectrum $\lambda_{max}$MeOH nm (1 g $\epsilon$) showed absorptions at 189 nm (4.39), 205.5 nm (4.51) and 259.5 nm (4.57). The molecular Formula $C_{22} H_{29} NO_3$ was derived from $^1$H NMR (400 MHZ, aceton-d6) and $^{13}$C NMR (100 MHZ, aceton-d6) data.

FIG. 1 shows NMR experiment results. Column 1 of the table is carbon atom serial number of the novel compound Formula II, Laetispicine.

Column 2 is $^{13}$C NMR data of chemical shifts number of the carbon atoms in the compound. Carbon atoms number 1 through number 11 formed a long carbon atom chain, among them the number 2 through number 5 carbon atoms are connected with two double bonds since the chemical shift numbers are larger than 100. The chemical shift number of carbon atom 9 and 10 were also larger than 100, indicating that there is also a double bond between them. There are double bonds among carbon atom number 1' through number 6', which formed a benzene structure according to the chemical shift numbers in FIG. 1, since the numbers are all larger than 100. There is no double bond in carbon atom number 6 through number 8 and carbon atom number 11, because the chemical shift numbers are smaller than 50 for those atoms.

Column 3 is $^1$H NMR data of chemical shifts number of the carbon atoms in the compound. If the chemical shift numbers are larger than 5, the numbers indicated that there are double bonds between the atoms of this part of the compound. If the numbers are smaller than 5, the data indicated that there are no double bonds between the atoms of the part of the compound. The chemical shift data of $^1$H NMR and $^{13}$C NMR are correspond very well in column 2 and column 3, confirming the molecular structure of the compound Formula II, Laetispicine.

The data in column 4 are coupling constants. The letter "d" meant double peaks, letter "dd" meant quadruple peaks, letter "t" meant triple peaks and letter "s" meant single peak.

The data in column 5 are correlations among the hydrogen atoms in the compound Formula II, Laetispicine.

EXPERIMENT 3

Mouse Forced Swimming Experiment

All animals were taken cared for according to Fudan University School of Pharmacy Animal Care and Welfare Guide Lines before, during and after experiments.

Mouse forced swimming experiment is by far the best animal model to screen anti-depression drugs. The experiment is designed to create a despaired situation for a mouse by confining the mouse in a container filled with water. Mouse in water will swim to safety. When the mouse cannot find a way out after it tried in the water in the container, it despaired of swimming. There is psychological difference of different mice in the situation. A calm mouse is still swimming and trying to find a way out of the container, while a despaired mouse swims relatively less (moves less). A depressed mouse despairs easily. The more depressed the mouse, the severer the despair. The mouse gets relieved from its depression hence despairs less if anti-depression drug is given before it is in the forced swimming experiment.

In this experiment, sixty mice were divided into 6 groups (10 mice in each group). (Referring to Table 1 and FIG. 2) Each mouse in experiment group 1 (Laetispicine 1) was given Laetispicine 50 milligram/kilogram body weight, each mouse in experiment group 2 (Laetispicine 2) was given Laetispicine 20 milligram/kilogram body weight, each mouse in experiment group 3 (Laetispicine 3) was given Laetispicine 10 milligram/kilogram body weight and each mouse in experiment group 4 (Laetispicine 4) was given Laetispicine 5 milligram/kilogram body weight. Fluoxetine (Prozac) was given 50 milligram/kilogram body weight to each mouse of positive control group (Fluoxetine), and placebo was given to each mouse of negative control group.

After receiving the drugs (or placebo) 1 hour later, mice were put into a glass container with a long and narrow opening. The dimension of the container is 30 cm height, filled with water to 15 cm deep. The motionless seconds, which indicates that the mouse might be depressed and despaired, stopped swimming at the time, of each mouse in the water were recorded for a total experiment time span of 4 minutes after it was allowed for 2 minutes of adaptation time in the new environment.

Table 1 and FIG. 2 show that Laetispicine significantly reduced the mouse depression. The results of anti-depression effect of Laetispicine were compared with the effect of Fluoxetine (Prozac) in mouse forced swimming experiments. It is observed that Laetispicine was five times effective than that of Prozac in terms of anti-depression. The differences of experiment data from different groups were statistically significant.

TABLE 1

| Test | Compound | Dose | Motionless Time (sec.) X ± SE |
|---|---|---|---|
| Control | None | | 190.89 ± 5.39 |
| Laetispicine 1 | Laetispicine | 50 mg/kg | 17.67 ± 5.33 |
| Laetispicine 2 | Laetispicine | 20 mg/kg | 50.11 ± 12.69 |
| Laetispicine 3 | Laetispicine | 10 mg/kg | 131.0 ± 8.86 |
| Laetispicine 4 | Laetispicine | 5 mg/kg | 158.78 ± 5.13 |
| Fluoxetine | Fluoxetine | 50 mg/kg | 113.44 ± 10.10 |

EXPERIMENT 4

Laetispicine Effect to Relieve Inflammation and Pain

All animals were taken cared for according to Fudan University School of Pharmacy Animal Care and Welfare Guide Lines before, during and after experiments.

The pain and inflammation relieving effect of Laetispicine has been studied by the mouse acetic acid squirming method. In this study, 30 male mice were selected; each of them weighed 20 grams. These mice were divided randomly into 3 groups: Laetispicine group (10 mice), aspirin group (10 mice), and control group (10 mice). Laetispicine of 20 milligram/kilogram body weight in vehicle solution was given to each of the ten mice in Laetispicine group. For a positive control, aspirin of 20 milligram/kilogram body weight in vehicle solution was given to each of the ten mice in aspirin group. Vehicle solution only was given to ten mice in control group (negative control group). One hour later, each mouse was given 0.2 milliliter of 1% acetic acid solution by injection to its abdominal cavity. After the mouse squirmed first time, every squirming of each of the mouse was counted in a period of 10 minutes. Experiment results, shown in Table 2, indicate that the inflammation and pain relieving effect of Laetispicine is equivalent to that of aspirin.

TABLE 2

| Test | Dose | Squirming X ± SE |
|---|---|---|
| Control | | 32.0 ± 6.57 |
| Laetispicine | 20 mg/kg | 16.7 ± 4.92 |
| Aspirin | 20 mg/kg | 16.8 ± 3.43 |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An essentially pure compound having the following structure of Formula II:

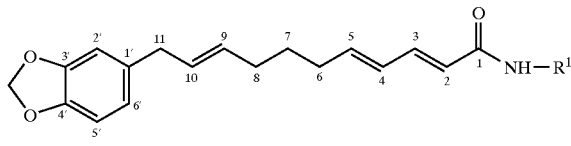

wherein $R^1$ is isobutyl ($-CH_2-CH(CH_3)_2$).

2. A pharmaceutical composition comprising a therapeutically effective amount of the essentially pure compound as claimed in claim 1 together with at least one pharmaceutically acceptable excipient.

3. The pharmaceutical composition of claim 2, wherein the composition is in oral form.

4. The pharmaceutical composition of claim 2, wherein the composition is in intravenous form.

5. The pharmaceutical composition of claim 2, wherein the composition is in subcutaneous form.

6. The pharmaceutical composition of claim 2, wherein the composition is in intramuscular form.

7. The pharmaceutical composition of claim 2, wherein the composition is in inhalation form.

8. The pharmaceutical composition of claim 2, wherein said composition is chemically modified as a therapeutically effective salt.

9. A method of obtaining an essentially pure compound of Formula II:

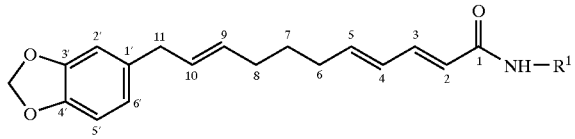

wherein $R^1$ is isobutyl ($-CH_2-CH(CH_3)_2$), comprising extracting and purifying the compound from *Piper laetispicum* of Piperaceae family.

10. A method of treating a disease characterized as mental disorder, comprising administering to a patient suffering from said disease a therapeutically effective amount of an essentially pure compound of Formula I:

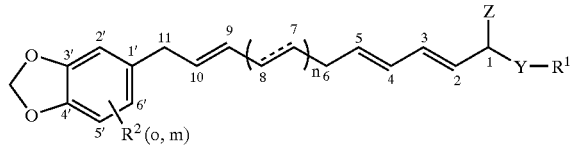

wherein $R^1$ is selected from the group consisting of hydrogen, $C_{1-10}$ alkyl and aromatic cyclic group, $R^2$ is selected from the group consisting of hydrogen, $OR^3$, $NH_2$, $NHR^3$, and halogen, Z is selected from the group consisting of $=O$, OH, $NHR^3$, SH, and $SR^3$, wherein $R^3$ is $C_{1-10}$ alkyl or aromatic cyclic group, $(C_7-C_8)_n$ includes at least one single bond or at least one double bond, n is an integer having a value of 0 to 10, and Y is selected from the group consisting of NH, $NR^3-$, O, and S.

11. The method of claim 10, wherein the disease is depression.

12. The method of claim 10, wherein the disease is psychopathic disease.

13. The method of claim 10, wherein the disease is Alzheimer's disease.

14. A method of alleviating a symptom characterized as inflammation and pain, comprising administering to a subject suffering from said symptom a therapeutically effective amount of an essentially pure compound of Formula I:

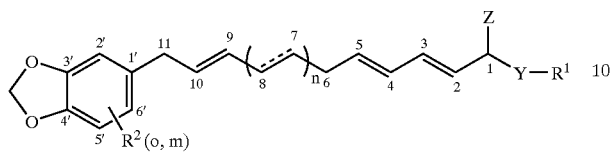

wherein $R^1$ is selected from the group consisting of hydrogen, $C_{1-10}$ alkyl and aromatic cyclic group, $R^2$ is selected from the group consisting of hydrogen, $OR^3$, $NH_2$, $NHR^3$, and halogen, Z is selected from the group consisting of $=O$, OH, $NHR^3$, SH, and $SR^3$, wherein $R^3$ is $C_{1-10}$ alkyl or aromatic cyclic group, $(C_7-C_8)_n$ includes at least one single bond or at least one double bond, n is an integer having a value of 0 to 10, and Y is selected from the group consisting of NH, $NR^3$—, O, and S.

* * * * *